(12) United States Patent
Geisslinger et al.

(10) Patent No.: US 9,103,919 B2
(45) Date of Patent: Aug. 11, 2015

(54) METHOD FOR TRANSMITTING REGISTER CONTENTS OF A CT DETECTOR WITH HIERARCHICAL HARDWARE STRUCTURE AND CT DETECTOR OF A CT SYSTEM

(71) Applicant: SIEMENS AKTIENGESELLCHAFT, Munich (DE)

(72) Inventors: Klaus Geisslinger, Leinburg (DE); Alexander Graf, Forchheim (DE); Edmund Götz, Effeltrich (DE); Stefan Hartmann, Eggolsheim (DE)

(73) Assignee: SIEMENS AKTIEGESELLSCHAFT, Munich (DE)

( * ) Notice: Subject to any disclaimer, the term of this patent is extended or adjusted under 35 U.S.C. 154(b) by 2 days.

(21) Appl. No.: 14/173,961

(22) Filed: Feb. 6, 2014

(65) Prior Publication Data

US 2014/0231663 A1 Aug. 21, 2014

(30) Foreign Application Priority Data

Feb. 18, 2013 (DE) .......................... 10 2013 202 572

(51) Int. Cl.
*G01T 1/00* (2006.01)
*G01T 1/16* (2006.01)
*G06F 9/30* (2006.01)
*G06F 19/00* (2011.01)

(52) U.S. Cl.
CPC ... *G01T 1/16* (2013.01); *G06F 9/30* (2013.01); *G06F 19/3406* (2013.01)

(58) Field of Classification Search
CPC ..................................... G01T 1/16; G01F 9/30
USPC .............................................. 250/363.04, 395
See application file for complete search history.

(56) References Cited

U.S. PATENT DOCUMENTS

2010/0278295 A1 11/2010 Kammerer et al.

FOREIGN PATENT DOCUMENTS

DE 102006002907 A1 7/2007
DE 102009019841 A1 11/2010

OTHER PUBLICATIONS

German Office Action for German Application 10 2013 202 572.6 Dated Oct. 1, 2013.
German Priority Document German Application 10 2013 202 572.6 filed Feb. 18, 2013.

*Primary Examiner* — David Porta
*Assistant Examiner* — Edwin Gunberg
(74) *Attorney, Agent, or Firm* — Harness, Dickey & Pierce, P.L.C.

(57) ABSTRACT

A method is disclosed for transmission of register contents of a CT detector with hierarchical hardware structure, wherein the first hierarchy level is formed by a control unit containing a register table for the read-out register contents of FPGAs lying lower down in the hierarchy and an intermediate register store for register contents to be written. With each new reading, the new register contents for FPGAs lying lower down in the hierarchy arriving during the respective preceding reading from the central control at the control unit are forwarded to the next hierarchy level. With each new reading, the register contents of all FPGAs lying lower down in the hierarchy are re-entered into the register table of the control unit. Finally, in the event of a readout command transferred asynchronously from the central control, the register contents are read out exclusively from the register table.

15 Claims, 4 Drawing Sheets

METHOD FOR TRANSMITTING REGISTER CONTENTS OF A CT DETECTOR WITH HIERARCHICAL HARDWARE STRUCTURE AND CT DETECTOR OF A CT SYSTEM

PRIORITY STATEMENT

The present application hereby claims priority under 35 U.S.C. §119 to German patent application number DE 102013202572.6 filed Feb. 18, 2013, the entire contents of which are hereby incorporated herein by reference.

FIELD

At least one embodiment of the invention generally relates to a method for transmitting register contents of a CT detector with hierarchical hardware structure between a central control and hardware components connected thereto with FPGAs, known as field-programmable gate arrays, wherein the FPGAs are divided into at least two hierarchy levels and write and readout processes of register contents are carried out cyclically over a hierarchy level during ongoing readings of the CT detector and asynchronously to the readings, write and readout commands are executed between the central control and the first hierarchy level of the FPGAs.

At least one embodiment of the invention further generally relates to a CT detector of a CT system which is controlled by a central control unit by write and readout commands of register contents, wherein the CT detector has a plurality of hardware components with FPGAs, known as field-programmable gate arrays, connected below one another in a hierarchy and the FPGAs each have registers with register contents.

BACKGROUND

A generally known CT detector has a number of hardware components with field-programmable gate arrays (=FPGAs). During operation a very wide variety of information (register contents) of the FPGAs must be written, read and evaluated by an external central control. This central control possesses only one communication link to the CT detector. For this reason internal connection paths between the FPGAs must be created in the CT detector, via which the central control can access all registers at any time. The central control in such cases requires a fixed reaction time of the CT detector. Since the internal connections for register accesses to the individual FPGAs are of different lengths and to some extent no direct access to the corresponding registers is possible, the reaction time also varies for different registers depending on their hierarchy level. In some cases the maximum reaction time demanded by the central control cannot be adhered to.

The data is transmitted between two hierarchy levels in such cases in accordance with the general timing behavior of a CT detector, by "readings". This means that, to overcome each hierarchy level, the duration of a reading (integration and readout time of the radiation measuring detector elements) is needed. In order to reach registers of hierarchically remote FPGAs, a corresponding multiple of the reading time is thus needed.

In parallel thereto there are internal control sequences in the CT detector which likewise simultaneously evaluate register contents from other FPGAs. For this purpose current register values of all FPGAs must always be available centrally and directly. A further requirement is the synchronous setting of a register in a number of HW components operating in parallel. This "broadcast" access from the central control should be made possible using only one register access.

In the known CT detectors, the central control must thus issue a number of update commands before the content of the desired register can then be accessed, possibly over a number of hierarchy levels below, and can be transmitted back until it is available. Access to all registers in the CT detector is thus only tedious and slow using this concept. Furthermore this procedure is very prone to errors, since for internal control sequences the individual register values have been inserted into the existing data transmission paths in order to rapidly and synchronously reach the register contents needed.

A direct access to FPGAs lying remotely in the hierarchy is not possible with prior-art detectors. Access must be initiated here in a complicated manner via a register set. This fact significantly reduces the bandwidth for accesses to such FPGAs. It also complicates the activation because ever more accesses are needed here until a register can be written or read respectively. Write or read accesses of the central control should however be able to be processed immediately.

SUMMARY

At least one embodiment of the invention is therefore directed to a method for transmitting register contents of hierarchically-linked FPGAs of a CT detector between a central control and hardware components connected thereto, which makes possible temporally-optimized access to the register contents of the FPGAs. Correspondingly, an improved CT detector of a CT system is also disclosed, in which a central control unit is controlled by write and readout commands from register contents of FPGAs.

Advantageous developments of the invention are the subject matter of dependent claims.

The inventors have recognized that the problem described above can be resolved by introducing a central register management in a control FPGA of the CT detector. The control FPGA possesses the direct physical connection to the central control. It is thus the first access partner for read or write requests from the central control.

The central register management in the control FPGA is embodied in this case so that it stores a complete map of all registers located in the CT detector internally in a table. To do this it continuously fetches the current register contents of all FPGAs via a separate high-speed connection automatically and through this can always guarantee the current register value in the control FPGA. If a read request now arrives from the central control this can immediately be serviced with the current values from the register map stored in the register table. For a write request the value to be written is transferred from the control FPGA into an intermediate register buffer and acknowledged immediately. A routine operating cyclically distributes the value to be written from the intermediate register buffer automatically via the internal connections to the correct FPGA.

In order to uniquely address the register addresses of the respective FPGAs outwards, the central register management issues a specific address offset for each FPGA. I.e. all CT detector registers are present below one another in a linear addressing scheme. The registers of the individual FPGAs can now be directly addressed. I.e. all registers can be written or read respectively with just one access. This entirely does away with complicated handling with update commands and register sets.

In order to access a number of FPGA registers simultaneously and synchronously an extra "broadcast" address range can be provided. If data is then written into this address range, the register management module automatically distributes this write command synchronously with the readings to all FPGAs concerned.

In summary this means that, for immediate provision of the most up-to-date register contents possible from FPGAs connected below one another in a hierarchy at the topmost hierarchy level—for example in a control unit or a control FPGA—a table (register table) is maintained, in which all register contents of FPGAs lying below said level in the hierarchy are reflected. For this purpose, in accordance with the data transmission cycle between two hierarchical levels in a CT detector which is synchronized with the integration and readout cycles (readings) of the detector, for each reading all register contents of the FPGAs lying one level lower are successively transmitted by one level upwards and as soon as they have reached the topmost level, are entered into the register table. This results in the newest possible register contents in the register table being available in the topmost hierarchy level in each case. This register table can be read out asynchronously by a central control unit and is thus available without delay.

If more than two hierarchy levels of FPGAs are implemented in the CT detector it is additionally proposed to introduce intermediate register tables into the FPGAs lying between the topmost and the lowest level, so that all register contents of all FPGAs lying at a hierarchically-lower level and connected to the respective FPGA are reflected. In this way the register contents can be transmitted one level upwards for each reading, so that the register contents of all FPGAs are present in the register table in each case, wherein the register contents of the FPGAs from the nth hierarchy level have an age of n readings.

In addition, in accordance with the correspondingly reversed scheme, new register contents to be written into the FPGAs are distributed over the hierarchy levels from top to bottom, wherein however not all register contents present in each case but only the register contents actually to be written, are transmitted in reading cycles from top to bottom. Accordingly memory space is merely made available for the respective register contents lying lower down in the hierarchy, in which the register contents to be written can be buffered exclusively with their corresponding register addresses.

In accordance with an embodiment of the invention illustrated above, the inventors propose a method for transmission of register contents of a CT detector with hierarchical hardware structure between a central control and hardware components connected thereto, each with at least one field-programmable gate array FPGA, wherein the FPGAs are subdivided into at least two hierarchy levels and write and readout processes of register contents are carried out cyclically over a hierarchy level during ongoing readings of the CT detector taking place and asynchronously to the readings, write and readout commands between the central control and the first hierarchy level of the FPGAs are carried out, wherein, in accordance with an embodiment of the invention the method comprises:

the first hierarchy level is formed by a control unit, which contains a register table for the read-out register contents of FPGAs lying lower in the hierarchy and a register buffer for register contents to be written, with each new reading, the new register contents arriving during the respective preceding reading from the central control at the control unit are forwarded for FPGAs lying lower down in the hierarchy to the next lower hierarchy level, with each new reading the register contents of all FPGAs lying lower in the hierarchy are re-entered into the register table of the control unit, and in the event of a readout command transferred asynchronously from the central control the register contents are read out exclusively from the register table.

Furthermore in another embodiment, the inventors propose, for the case of a hierarchically more complex structure of the CT detector, a method comprising:

the FPGAs are divided into at least three hierarchy levels with at least one intermediate level located between the first and the last hierarchy level, register contents of the FPGAs lying lower in the hierarchy are written into the at least one intermediate level into at least one intermediate register buffer in each case, and are transmitted per reading to the next lower hierarchy level, and also the read-out register contents of the FPGAs lying lower down in the hierarchy are re-entered into a buffer register table in each case and are transmitted to the next higher hierarchy level per reading.

As well as embodiments of the inventive method, the inventors also propose the improvement of a CT detector of a CT system which is controlled by a central control unit by write and readout commands of register contents, wherein the CT detector has a plurality of hardware components with field-programmable gate arrays FPGA connected hierarchically below one another and the FPGAs each have registers with register contents. In accordance with an embodiment of the invention, the improvement includes at least one control unit being provided in a first hierarchy level, which has a register table for read-out register contents of FPGAs lying lower down in the hierarchy and a register buffer for register contents to be written.

For the case of a hierarchically more complex embodiment of the CT detector, the inventors also propose that at least:

the FPGAs are divided into at least three hierarchy levels, with at least one intermediate level lying between the first and the last hierarchy level, in the at least one intermediate level an intermediate register buffer is provided in a least one FPGA for register contents of the FPGAs lying lower down in the hierarchy in each case, and in the at least one intermediate level at least one intermediate register table is stored in at least one FPGA for the read-out register contents of the FPGAs lying below it.

BRIEF DESCRIPTION OF THE DRAWINGS

The invention is explained below in greater detail with reference to example embodiments with the aid of the figures, wherein only the features necessary for understanding the invention are shown. The following reference numbers are used: 1: CT System; 2: X-ray emitter; 3: Detector; 4: X-ray emitter; 5: Detector; 5.1: Control FPGA; 5.1.1: Register table; 5.1.2: Register buffer; 5.2.1-5.2.$n$; 5.3.1-5.3.$m$: FPGAs lying one level further down; 5.2.2.1, 5.2.3.1: Intermediate register table; 5.2.2.2, 5.2.3.2: Intermediate register buffer; 6: Gantry housing; 7: Patient; 8: Patient couch; 9: System axis; 10: Control and processing unit; DE1-DEk: Detector element; DMAR: control and processing circuit board; SBPLh: Signal Back Planes high; SBPLl: Signal Back Planes low; MBPL1-MBPLm: Module Back Plane; Prg1-Prgn: Computer programs; R: Registers; ZM: Central register management; I, II, III: Hierarchy levels.

In the figures.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with an embodiment of the invention illustrated above, the inventors propose a method for transmission of register contents of a CT detector with hierarchical hardware structure between a central control and hardware components connected thereto, each with at least one field-programmable gate array FPGA, wherein the FPGAs are subdivided into at least two hierarchy levels and write and readout processes of register contents are carried out cyclically over a hierarchy level during ongoing readings of the CT detector taking place and asynchronously to the readings, write and readout commands between the central control and the first hierarchy level of the FPGAs are carried out, wherein, in accordance with an embodiment of the invention the method comprises:

the first hierarchy level is formed by a control unit, which contains a register table for the read-out register contents of FPGAs lying lower in the hierarchy and a register buffer for register contents to be written, with each new reading, the new register contents arriving during the respective preceding reading from the central control at the control unit are forwarded for FPGAs lying lower down in the hierarchy to the next lower hierarchy level, with each new reading the register contents of all FPGAs lying lower in the hierarchy are re-entered into the register table of the control unit, and in the event of a readout command transferred asynchronously from the central control the register contents are read out exclusively from the register table.

Through an embodiment of this inventive method it is ensured that all of the most up-to-date possible register contents of all FPGAs lying therebelow in the hierarchy are maintained in an asynchronously accessible component of the detector, without the request command being forwarded initially for a request across a number of readings over the hierarchy levels and the requested register contents then having to be tediously successively transmitted upwards in the hierarchy. A drastic gain in reaction time is thus produced.

Furthermore in another embodiment, the inventors propose, for the case of a hierarchically more complex structure of the CT detector, a method comprising:

the FPGAs are divided into at least three hierarchy levels with at least one intermediate level located between the first and the last hierarchy level, register contents of the FPGAs lying lower in the hierarchy are written into the at least one intermediate level into at least one intermediate register buffer in each case, and are transmitted per reading to the next lower hierarchy level, and also the read-out register contents of the FPGAs lying lower down in the hierarchy are re-entered into a buffer register table in each case and are transmitted to the next higher hierarchy level per reading.

It is also advantageous for a bidirectional transmission of register contents of neighboring hierarchy levels to take place during each reading.

Furthermore the register contents of all FPGAs linked and lying lower down in the hierarchy should be stored in each register table and in the case of more than two hierarchy levels, the register contents of all FPGAs linked and lying further down in the hierarchy levels should also be stored in each intermediate register table.

As well as embodiments of the inventive method, the inventors also propose the improvement of a CT detector of a CT system which is controlled by a central control unit by write and readout commands of register contents, wherein the CT detector has a plurality of hardware components with field-programmable gate arrays FPGA connected hierarchically below one another and the FPGAs each have registers with register contents. In accordance with an embodiment of the invention, the improvement includes at least one control unit being provided in a first hierarchy level, which has a register table for read-out register contents of FPGAs lying lower down in the hierarchy and a register buffer for register contents to be written.

A development of the CT detector can advantageously include at least one device being provided through which, during operation, with each new reading of the CT detector, the new register contents arriving during the respective preceding reading from the central control at the control unit are forwarded for FPGAs lying lower down in the hierarchy to the next lower hierarchy level.

In concrete terms the functionally defined devices specified in this document can for example include corresponding software which, during operation of the CT detector, executes the required functions. As an alternative such programming, as is typical for FPGAs, can however also be executed by hard-wired circuits.

It is further also proposed that at least one device is present, through which, with each new reading, the register contents of all FPGAs lying lower down in the hierarchy are re-entered into the register table of the control unit.

In addition it is also proposed that at least one device is provided, through which, in the event of a readout command transmitted asynchronously from the central control, the register contents are read out exclusively from the register table of the control unit.

For the case of a hierarchically more complex embodiment of the CT detector, the inventors also propose that at least:

the FPGAs are divided into at least three hierarchy levels, with at least one intermediate level lying between the first and the last hierarchy level, in the at least one intermediate level an intermediate register buffer is provided in a least one FPGA for register contents of the FPGAs lying lower down in the hierarchy in each case, and in the at least one intermediate level at least one intermediate register table is stored in at least one FPGA for the read-out register contents of the FPGAs lying below it.

Through this embodiment, intermediate register tables and intermediate register buffers are maintained in the intermediate levels, i.e. in all hierarchical levels with the exception of the first and the last level, in which in each case register contents originating from the FPGAs arranged lower down in the hierarchy or register contents to be written are buffered, in order to be able to transmit them with the next reading in each case to the next hierarchy level.

It is also advantageous for the register contents of all FPGAs linked and lying lower down in the hierarchy to be stored in each register table and furthermore for the register contents of all FPGAs linked and lying lower down in the hierarchy to be stored in each intermediate register table.

Figure 1:
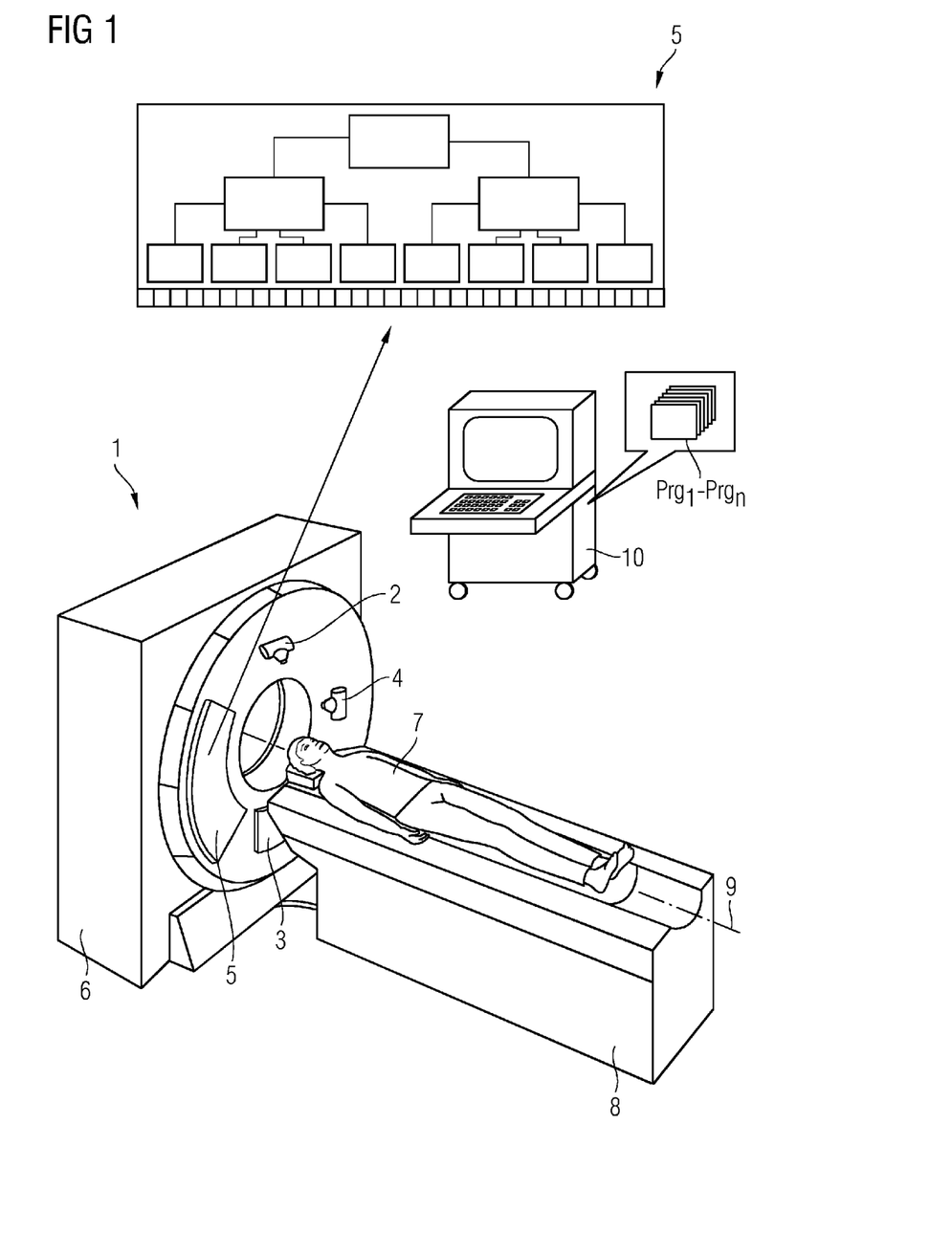
FIG. 1 shows a CT system with an embodiment of an inventive CT detector.

FIG. 1 shows a CT system 1, with a structure known per se, including a gantry housing 6, a gantry lying therein, on which one or more—here two—CT detectors 3 and 5 and two x-ray emitters 2 and 4 are arranged opposite the CT detectors in each case. FIG. 1 also shows a patient couch 8, on which a patient 7 can be disposed, in order to be moved for scanning through the measurement field between the rotating emitter/detector systems.

The CT system is controlled by a processing and control unit 10 which also handles the task of a central control for the CT detector or CT detectors. Above the CT system 1, to illustrate the inventive layout of the CT detector, a symbolic sectional view through the 32-row CT detector 5 is shown separately. The layout of the CT detector corresponds in this case to the structures of an inventive CT detector described in greater detail below with FIGS. 3 and 4.

As stated above, an embodiment of the invention lies in reflecting registers of FPGAs lying lower down in the hierarchy and not able to be addressed directly in a topmost hierarchy level and continuously updating them, so that there can be access to the mirrored register contents by the central control at all times and without taking account of the cyclic readings. As devices for this purpose, the programs Prg1-Prgn can be embodied in accordance with the central control and the programming of the FPGAs.

Figure 2:
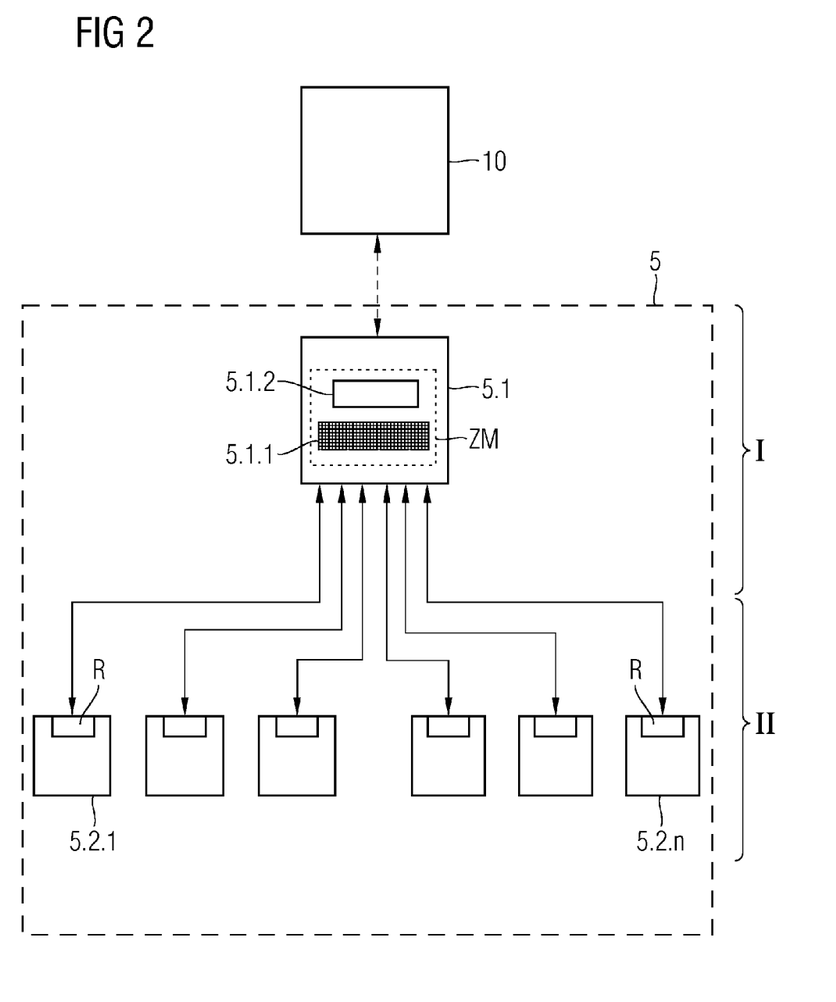
FIG. 2 shows a CT detector with hierarchically arranged FPGAs in two hierarchy levels I to II.

FIG. 2 shows a schematic of an embodiment of an inventively embodied CT detector 5. The CT detector 5 is in communication with a central control 10 via a communication link, via which on the one hand register contents to be written can be transmitted from the central control 10 to the detector 5, on the other hand register contents of the FPGAs communicating hierarchically in the detector via further communication links can be requested. In the version shown here the CT detector 5 has two hierarchy levels I and II, wherein the first, topmost hierarchy level I is formed by a control FPGA 5.1.

In accordance with an embodiment of the invention, this control FPGA 5.1 has a central register management ZM with a register table 5.1.1 for mirroring all FPGAs lying lower in the hierarchy and a register buffer 5.1.2 for buffering register contents of which the values have been transferred by the central control unit to the control FPGA 5.1 for entry into the registers of the FPGAs lying lower down in the hierarchy.

If the control FPGA 5.1 receives new register contents to be written from the central control, these are buffered in the register buffer 5.1.2 until the next reading and then, with the next reading cycle, a hierarchical level is transmitted onwards to the addressed FPGA and written into the register there.

If the control FPGA 5.1 receives a request relating to current register contents of one of the registers R of the FPGAs 5.2.1 to 5.2.n lying one level lower down in the hierarchy, this register contents does not have to be fetched separately, but can be taken directly from the register table 5.1.1. In this way an extremely fast external access to the register contents of hierarchically-linked FPGAs is made possible.

Figure 3:
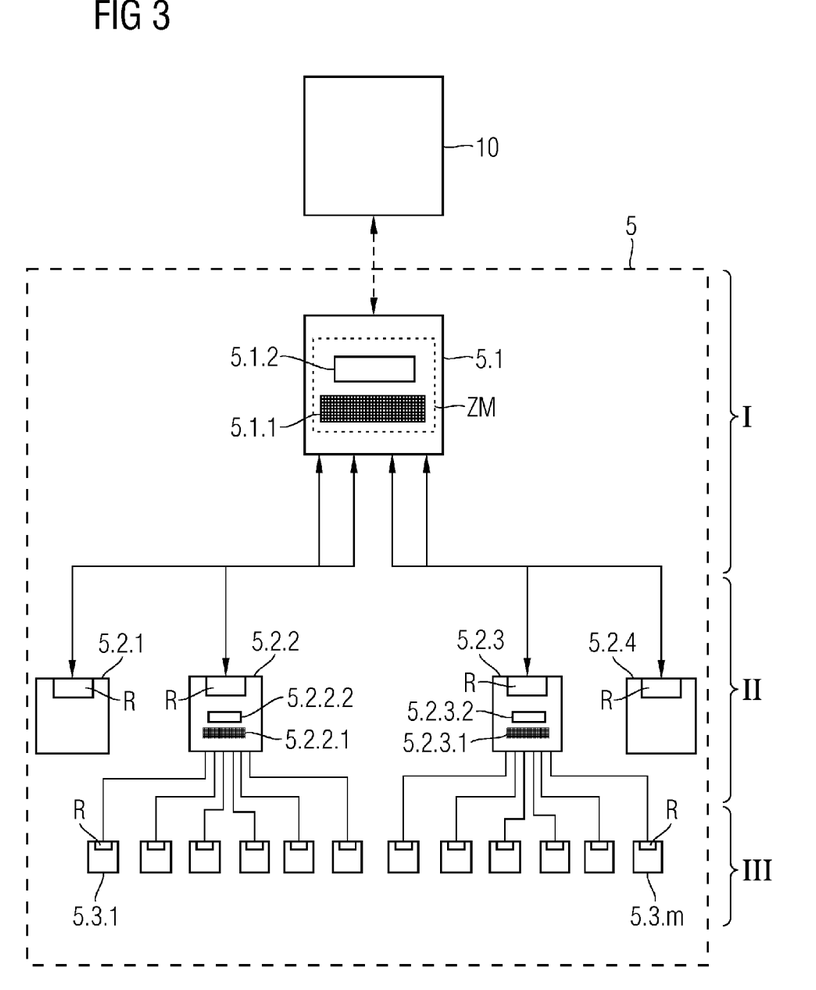
FIG. 3 shows a CT detector with hierarchically arranged FPGAs in three hierarchy levels I to III and FIG. 4 shows a CT detector with a hierarchical structure in accordance with FIG. 3 with hardware-component-related subdivision.

In the case of a more extensive hierarchy with three or more hierarchy levels it is necessary to provide additional buffering options for register contents to be transmitted. A typical embodiment of the CT detector with three hierarchy levels is shown in FIG. 3. Basically the diagram corresponds to that of FIG. 2, however, as well as FPGAs 5.2.1 to 5.2.4, additional FPGAs 5.3.1 to 5.3.m are also present there, which form a third hierarchy level III and are linked in each case to one of the FPGAs 5.2.2 or 5.2.3 by communication lines. Each FPGA of a level which is not at the end of a hierarchy, which communicates with further FPGAs of a lower level—here 5.2.2 and 5.2.3—also has an intermediate register table 5.2.2.1 or 5.2.3.1 and an intermediate register buffer 5.2.2.2 or 5.2.3.2.

With a CT detector equipped in this way, and with the aid of the intermediate register tables including correspondingly embodied programming present in the FPGAs of the non-end-level hierarchy stages, successively and with the readings the register table arranged at the top of the hierarchy can continuously be permanently updated, so that for the register contents of all, even the hierarchically remote FPGAs, there can be ad-hoc requests from the central control, without readout commands initially having to be transmitted "downwards" via a number of readings, and then the requested register contents having to be transmitted "upwards". The timing behavior during the request of the register contents is thus significantly speeded up.

Figure 4:
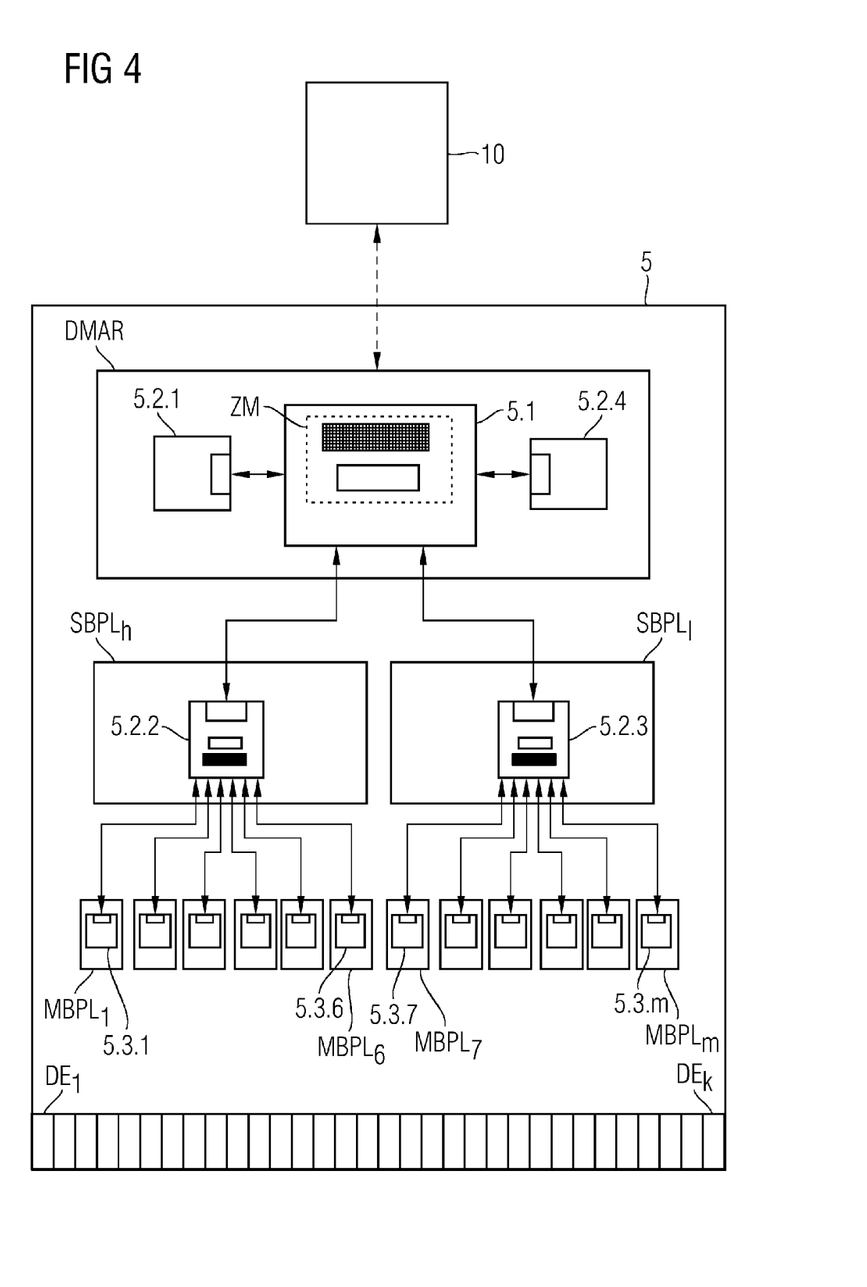

FIG. 4 shows an example of a hardware-side structuring of an embodiment of the inventive CT detector from FIG. 3 once more, with an explicit presentation of the hardware components. The detector 5 has in its hardware-side layout a monitoring and control board DMAR, in which the control FPGA 5.1 with the central register management ZM—which represents the first hierarchy level—and two further FPGAs 5.2.1 and 5.2.4 from the second hierarchy level are located. Furthermore two "signal backplanes" SBPLh and SBPLl—the indices h and l stand for high and low—are connected directly via data lines to the monitoring and control board DMAR, wherein each signal backplane represents a separate hardware component. Each signal backplane SBPLh and SBPLl has a hierarchical data connection in its turn to a number of—here six—module backplanes MBPL1 to MBPL6 or MBPL7 to MBPLm. In this case an FPGA 5.3.1 to 5.3.m is integrated into each module backplane MBPL1 to MBPLm. For reasons of clarity the internal layout of the individual FPGAs is not shown in detail with reference numbers in this figure but is only shown by way of the drawing. It corresponds to the layout of the FPGAs from FIG. 3 however.

In addition, a series of detector elements DE1 to DEk is also shown at the bottom of the detector 5. It is pointed out however that the hardware layout shown above is not used for reading out the detector elements but for control. The reading out of the register contents described in this document thus exclusively relates to the control of the CT detector and does not transmit any dose information. The dose data is read out from the detector elements via separate data paths not shown here.

Thus a method for transmission of register contents of a CT detector with a hierarchical hardware structure and a CT detector of this type is proposed with an embodiment of the invention, wherein the first hierarchy level is formed by a control unit, containing a register table for the read-out register contents of FPGAs lying lower down in the hierarchy and an intermediate register buffer for register contents to be written, with each new reading the new register contents for FPGAs lying lower down in the hierarchy arriving during the respective preceding reading from the central control at the control unit being forwarded to the next hierarchy level, with each new reading the register contents of all FPGAs lying lower in the hierarchy being entered again into the register table of the control unit, and in the event of a readout command transferred asynchronously from the central control the register contents are exclusively read out from the register table.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. A method for transmitting register contents of a CT detector with hierarchical hardware structure between a central control and hardware components connected thereto, each with at least one field-programmable gate array (FPGA), wherein the FPGAs are divided into at least two hardware levels and, during ongoing readings of the CT detector, write and readout processes of register contents are performed cyclically beyond a hierarchy level and asynchronously to the readings, write and readout commands between the central control and the first hierarchy level of the FPGAs are executed, the method comprising:
    forming the first hierarchy level by a control unit which contains a register table for the read-out register contents of FPGAs lying relatively lower down in the hierarchy and a register buffer for register contents to be written;
    forwarding to the next respective hierarchy level, with each respective new reading, new register contents arriving during respective preceding reading from the central control at the control unit for FPGAs lying relatively lower down in the hierarchy;
    re-entering into the register table of the control unit, with each respective new reading, the register contents of all FPGAs lying relatively lower down in the hierarchy; and
    reading out, in an event of a readout command transferred asynchronously from the central control, the register contents exclusively from the register table.

2. The method of claim 1, further comprising:
    dividing the FPGAs into at least three hierarchy levels with at least one intermediate level lying between the first and last hierarchy level;

writing register contents of the respective FPGAs lying relatively further down in the hierarchy, into the at least one intermediate level into an intermediate register buffer in each case and transferring the written register contents of the respective FPGAs lying relatively further down in the hierarchy, for each respective reading, to the next lower hierarchy level; and entering new read-out register contents of the FPGAs lying below said level in the hierarchy, per respective reading, into an intermediate register table and transferring the entered read-out register contents of the FPGAs lying below said level in the hierarchy, per respective reading, to the next-higher hierarchy level.

3. The method as of claim 1, wherein, during each respective reading, a bidirectional transmission of register contents of neighboring hierarchy levels.

4. The method of claim 1, wherein the register contents of all FPGAs connected and lying relatively lower down in the hierarchy are stored in each respective register table.

5. The method of claim 2, wherein the register contents of all FPGAs connected and lying relatively lower down in the hierarchy are stored in each respective intermediate register table.

6. A CT detector of a CT system, controllable by a central control unit by write and readout commands from register contents, the CT detector comprising:
a plurality of hardware components with field-programmable gate arrays (FPGAs) connected hierarchically below one another, the FPGAs each including registers with register contents, wherein at least one control unit is provided in a first hierarchy level, including a register table for read-out register contents of FPGAs lying relatively lower down in the hierarchy and a register buffer for register contents to be written.

7. The CT detector of claim 6, wherein at least one device is provided through which, during operation, with each new respective reading of the CT detector, the new register contents for FPGAs lying respectively lower down in the hierarchy arriving during the respective preceding reading from the central control at the control unit are forwarded to the respective next-lower hierarchy level.

8. The CT detector of claim 6, wherein at least one device is provided, through which, with each respective new reading, the register contents of all FPGAs lying relatively lower down in the hierarchy are re-entered into the register table of the control unit.

9. The CT detector of claim 6, wherein at least one device is provided, through which, in the event of a readout command transferred asynchronously from the central control, the register contents are read out exclusively from the register table of the control unit.

10. The CT detector of claim 6, wherein the FPGAs are divided into at least three hierarchy levels with at least one intermediate level lying between the first and last respective hierarchy level, wherein, in the at least one intermediate level in at least one FPGA, at least one intermediate register buffer is provided for register contents of the FPGAs lying respectively lower down in the hierarchy level, and wherein, in the at least one intermediate level in at least one FPGA, at least one intermediate register table is stored for the read-out register contents of the FPGAs lying below it.

11. The CT detector of claim 6, wherein the register contents of all FPGAs connected and lying relatively lower down in the hierarchy are stored in each respective register table.

12. The CT detector of claim 10, wherein the register contents of all FPGAs connected and lying relatively lower down in the hierarchy are stored in each respective intermediate register table.

13. The method as of claim 2, wherein, during each respective reading, a bidirectional transmission of register contents of neighboring hierarchy levels.

14. The CT detector of claim 7, wherein at least one device is provided, through which, with each respective new reading, the register contents of all FPGAs lying relatively lower down in the hierarchy are re-entered into the register table of the control unit.

15. The CT detector of claim 10, wherein the register contents of all FPGAs connected and lying relatively lower down in the hierarchy are stored in each respective intermediate register table.

* * * * *